(12) United States Patent
Koelmel

(10) Patent No.: US 9,908,158 B2
(45) Date of Patent: Mar. 6, 2018

(54) AIR FLOW MECHANISM FOR IMAGE CAPTURE AND VISION SYSTEMS

(71) Applicant: AMETEK, INC., Berwyn, PA (US)

(72) Inventor: Volker Koelmel, Neuenburg (DE)

(73) Assignee: AMETEK, INC., Berwyn, PA (US)

( * ) Notice: Subject to any disclaimer, the term of this patent is extended or adjusted under 35 U.S.C. 154(b) by 0 days.

(21) Appl. No.: 14/202,202

(22) Filed: Mar. 10, 2014

(65) Prior Publication Data

US 2015/0251227 A1   Sep. 10, 2015

(51) Int. Cl.
| | | |
|---|---|---|
| *B08B 5/02* | (2006.01) | |
| *G01N 21/15* | (2006.01) | |
| *G01N 21/88* | (2006.01) | |
| *G03B 17/56* | (2006.01) | |
| *H04N 5/225* | (2006.01) | |

(52) U.S. Cl.
CPC .............. *B08B 5/02* (2013.01); *G01N 21/15* (2013.01); *G01N 21/88* (2013.01); *G03B 17/568* (2013.01); *H04N 5/2251* (2013.01); *G01N 2021/151* (2013.01)

(58) Field of Classification Search
CPC ............ G02B 27/0006; G02B 23/2492; G01N 21/15; B60R 1/06
USPC ....................... 348/82–95, 373; 359/507–509
See application file for complete search history.

(56) References Cited

U.S. PATENT DOCUMENTS

| | | | | |
|---|---|---|---|---|
| 3,321,265 A | * | 5/1967 | Clave et al. ................... | 359/509 |
| 5,115,342 A | * | 5/1992 | Rowe et al. ................... | 359/509 |
| 5,313,685 A | | 5/1994 | Kramer et al. | |
| 5,331,151 A | * | 7/1994 | Cochran et al. .......... | 250/223 R |
| 5,490,300 A | | 2/1996 | Horn | |
| 5,592,217 A | * | 1/1997 | Hirvonen et al. .............. | 348/83 |
| 5,593,499 A | | 1/1997 | Stans et al. | |
| 5,831,668 A | * | 11/1998 | Hirvonen et al. .............. | 348/83 |
| 6,890,080 B2 | | 5/2005 | Kalley et al. | |

(Continued)

FOREIGN PATENT DOCUMENTS

| | | |
|---|---|---|
| CN | 201516433 U | 6/2010 |
| EP | 1516677 A1 | 3/2005 |

(Continued)

OTHER PUBLICATIONS

Lee, et al., "A Study on the Air Knife Flow With Coanda Effect", "Journal of Mechanical Science and Technology", Jan. 1, 2007, pp. 2214-2220, vol. 21, Published in: KR.

*Primary Examiner* — Christopher K Peterson
(74) *Attorney, Agent, or Firm* — RatnerPrestia

(57) ABSTRACT

This invention provides a mechanism for clearing debris and vapors from the region around the optical axis of a vision system that employs a directed airflow in the region. The airflow is guided by an air knife that surrounds a viewing gap placed in front of the camera optics. The air knife delivers airflow in a manner that takes advantage of the Coanda effect to generate an airflow that prevents infiltration of debris and contaminants into the optical path. Illustratively, the air knife defines a geometry that effectively multiplies the delivered airflow approximately fifty times (twenty-five times on each of two air-knife sides) that of the supplied compressed air. This provides an extremely strong air curtain along the scan direction that essentially blocks infiltration of environmental contamination to the optics of the camera.

22 Claims, 6 Drawing Sheets

(56) References Cited

U.S. PATENT DOCUMENTS

| | | | |
|---|---|---|---|
| 8,223,200 B1* | 7/2012 | Benttine et al. | 348/89 |
| 2008/0030722 A1* | 2/2008 | Barker et al. | 356/138 |
| 2008/0285132 A1* | 11/2008 | O'Kane | 359/509 |
| 2009/0033743 A1* | 2/2009 | Gruber-Nadlinger et al. | 348/86 |
| 2010/0120350 A1 | 5/2010 | Pucciani | |
| 2011/0024528 A1* | 2/2011 | Pucciani | 239/597 |
| 2013/0062228 A1* | 3/2013 | Danilov | 206/216 |
| 2013/0194379 A1* | 8/2013 | Baleine et al. | 348/36 |
| 2013/0194411 A1* | 8/2013 | Baleine et al. | 348/82 |

FOREIGN PATENT DOCUMENTS

| | | |
|---|---|---|
| EP | 2482059 A2 | 8/2012 |
| JP | 2013-228358 A | 11/2013 |
| WO | 2005102544 A1 | 3/2005 |

\* cited by examiner

AIR FLOW MECHANISM FOR IMAGE CAPTURE AND VISION SYSTEMS

FIELD OF THE INVENTION

This invention relates to machine vision systems and more particularly to vision systems employed in harsh, contaminant-rich and/or moist environments.

BACKGROUND OF THE INVENTION

Machine vision systems (also termed "vision systems") that perform measurement, inspection, alignment of objects and/or decoding of symbology (e.g. bar codes) are used in a wide range of applications and industries. These systems are based around the use of an image sensor, which acquires images (typically grayscale or color, and in one, two or three dimensions) of the subject or object, and processes these acquired images using an on-board or remote, interconnected vision system processor. The processor generally includes both processing hardware and non-transitory computer-readable program instructions that perform one or more vision system processes to generate a desired output based upon the image's processed information. This image information is typically provided within an array of image pixels each having various colors and/or intensities. In the example of a symbology (barcode) reader, the user or automated process acquires an image of an object that is believed to contain one or more barcodes. The image is processed to identify barcode features, which are then decoded by a decoding process and/or processor obtain the inherent alphanumeric data represented by the code. In other types of vision systems, various vision system tools (e.g. edge detectors, calipers, blob analysis) are employed by the system processor to detect edges and other features that allow for recognition of object features, and the determination of desired information based upon these features—for example whether the object is defective or whether it is properly aligned. Likewise, vision system tools can be used to detect imperfections and/or defects in an object—such as in a surface inspection arrangement.

In a vision system, a major component is the vision system camera assembly. The camera assembly typically includes a lens (optics) and an imager (or "sensor") that provides the array of image pixel information. The vision system processor receives the pixel data from the imager/sensor and processes it to derive useful vision system information about the imaged scene and/or object. The vision system processor and related components (e.g. data memory, decoders, etc.) can be provided within the camera assembly's physical housing or enclosure, or some or all of these vision processing components can be mounted remotely (e.g. within a PC, or other remote, self-contained processing system), and linked by a wired or wireless interconnect.

The camera assembly can be arranged to direct light from the scene through an optic that focuses the light on either a 2D image sensor or a 1D image sensor. A 2D arrangement typically employs a cylindrical barrel lens arrangement, or the like, to focus the light onto an array of sensor pixels arranged in a grid of N×M (e.g. height/width), while a 1D arrangement, also termed a "line scan" camera includes a sensor arranged as a single row of N pixels arranged at an appropriate width. Image acquisition is in the form of a "line" or "row" of pixels, with the acquisition of each row typically synchronized by an encoder or other motion-sensing device that registers a series of acquired lines. Thus, the image is typically acquired along a width direction that is transverse to the motion direction. The overall image of the surface comprises a continuous grouping of line images registered to a particular length increment based upon the motion of the surface with respect to the camera. Note that either, or both, the camera and imaged surface can be in motion (i.e. providing "relative" motion with respect to each other).

In various line-scan environments, as well as other imaging environments—for example those employing a 2D image sensor—the vision system is deployed in an environment that can be relatively harsh. For example, the environment can include airborne dust, chips, vapors (e.g. paint, ink, steam, etc.) and other contaminants that can obscure the image or accrete to the imager optics. Such occluding debris can temporarily or permanently (i.e. until it is cleaned from the optics) degrade or even blind the vision system.

SUMMARY OF THE INVENTION

This invention overcomes disadvantages of the prior art by providing a mechanism for clearing debris and vapors from the region around the optical axis of a vision system that employs a directed airflow in the region. The airflow is guided by an air knife that surrounds a viewing gap placed in front of the camera optics. The air knife delivers airflow in a manner that takes advantage of the Coanda effect to generate an airflow that prevents infiltration of debris and contaminants into the optical path. Illustratively, the air knife defines a geometry that effectively multiplies the delivered airflow approximately fifty times that of the supplied compressed air when both air knife sides are activated (i.e. twenty-five times per air knife side). This provides an extremely strong air curtain along the scan direction that essentially blocks infiltration of environmental contamination to the optics of the camera.

In an illustrative embodiment, a vision system for imaging a scene containing contaminants includes a camera assembly having an image sensor, and optics that define an optical axis and a field of view. The camera assembly and optics can be a line scan camera and the image sensor can be a 1D sensor arrangement. An air knife assembly is provided, and includes (a) a first angled surface that extends inwardly and upwardly from a bottom of the first angled surface to a top of the first angled surface; (b) a slot that extends through the air knife assembly along the optical axis so as to allow the scene to be imaged through the slot; and (c) a first air flow passage located adjacent to the bottom of the first angled surface. The bottom of the first angled surface is constructed and arranged to direct air flow from the first air flow passage along an exterior face of the first angled surface. The top of the first angled surface is constructed and arranged to redirect air flow from the exterior face of the first angled surface into the field of view. Illustratively, the system includes a vision system processor operatively connected to the image sensor for performing vision system tasks on image data transmitted from the image sensor. Also, illustratively, the air knife assembly has a second angled surface, on an opposite side with respect to the optical axis from a side having the first angled surface. The second angled surface extends inwardly and upwardly from a bottom of the second angled surface to a top of the second angled surface. A corresponding second air flow passage is located adjacent to the bottom of the second angled surface. The bottom of the second angled surface is constructed and arranged to direct air flow from the second air flow passage along an exterior face of the second angled surface and the top of the second angled surface being constructed and arranged to redirect air flow from the exterior face of the second angled surface into the field of view. Illustratively, the first angled surface and the second angled surface are each located on a core section. The core section is operatively connected to (a) a first side member that defines the first air flow passage and (b) a second side member that defines the second air flow passage. The first side member can overlie a first air chamber within the core section, with the first air chamber extending at least part of a length of the core section. Likewise, the second side member can overlie a second air chamber within the core section, with the second air chamber extending at least part of a length of the core section on a side of the slot opposite the first air chamber. At least one of the first air chamber and the second air chamber is operatively connected to a conduit (a tube) that directs pressurized air into the at least one of the first air chamber and the second air chamber. To generate appropriate air flow into the field of view, the top of the first angled surface defines a first radius and the bottom of the first angled surface defines a second radius. Corresponding radii can also be provided to the top and the bottom of the second angled surface. The top of the first angled surface (and/or the second angled surface) can be connected to a vertical wall that confronts the slot, and that extends upwardly from the first radius. This vertical wall can also define a bevel at a top edge thereof that enhances air flow toward the field of view to deflect contaminants away from the slot.

BRIEF DESCRIPTION OF THE DRAWINGS

The invention description below refers to the accompanying drawings, of which.

DETAILED DESCRIPTION

Figure 1:
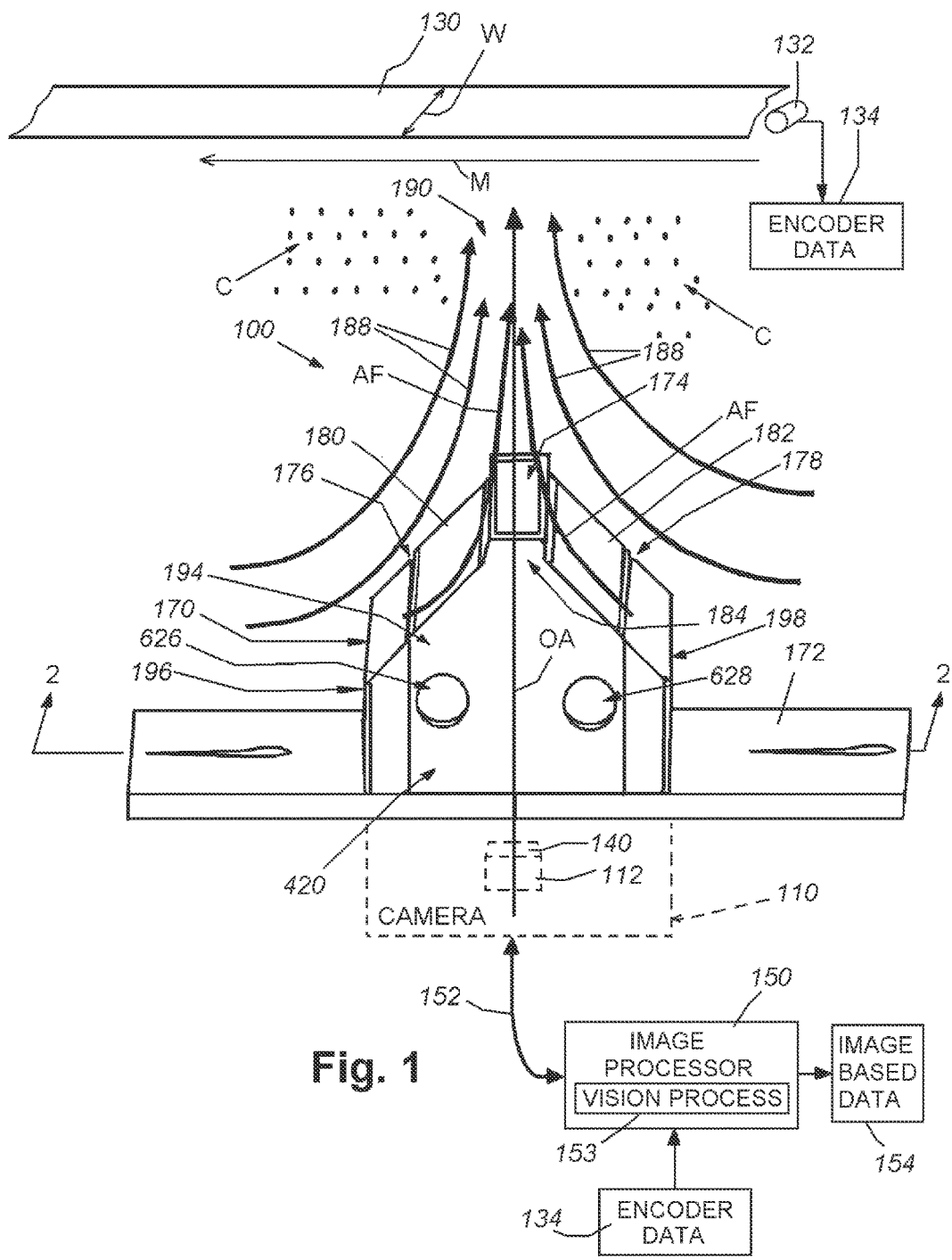
FIG. 1 is a perspective view of a vision system scanning a surface in relative motion, employing an air knife assembly according to an illustrative embodiment.
Figure 2:
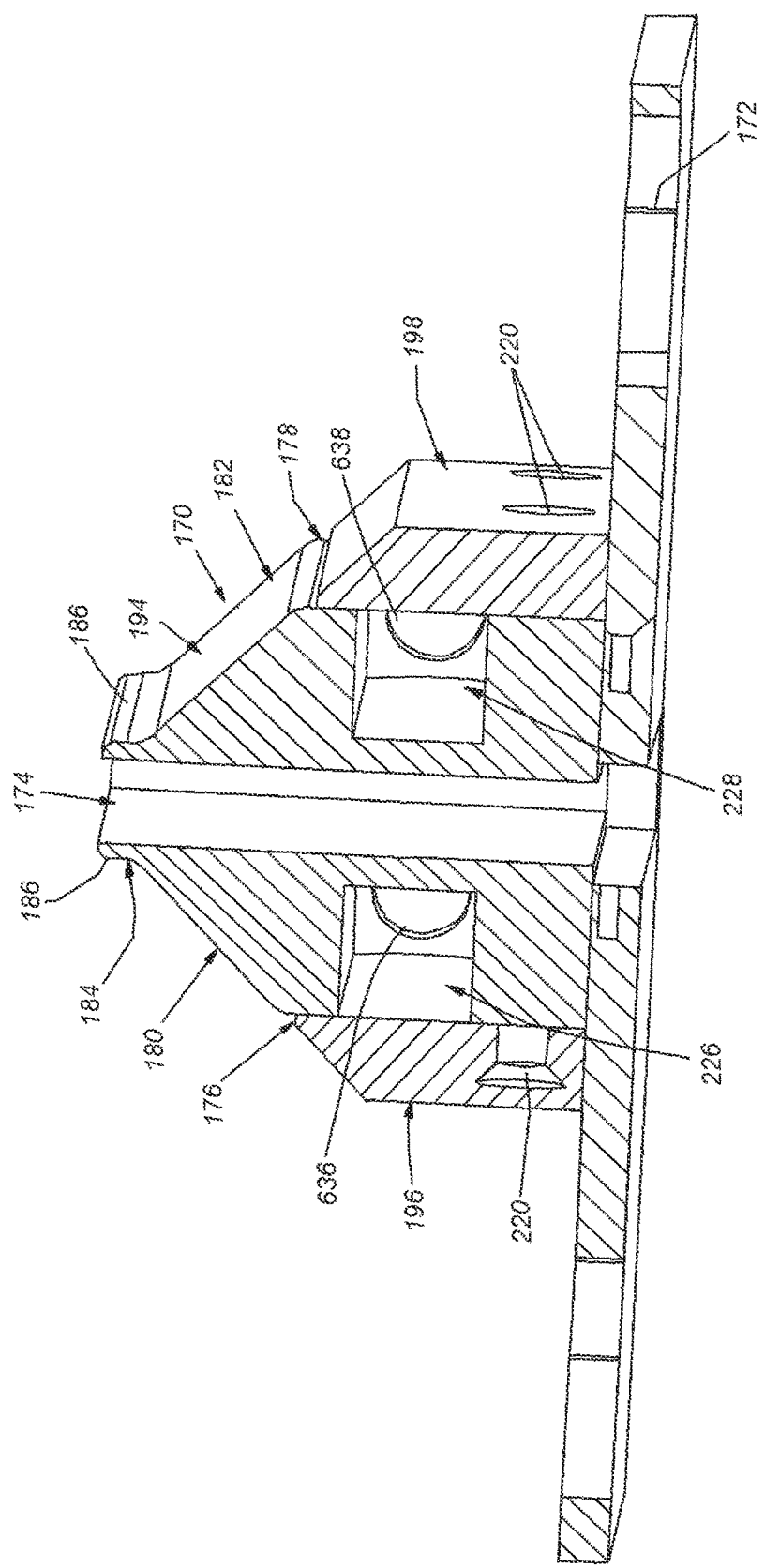
FIG. 2 is a perspective cross section of the air knife assembly taken along line 2-2 of FIG. 1.
Figure 3:
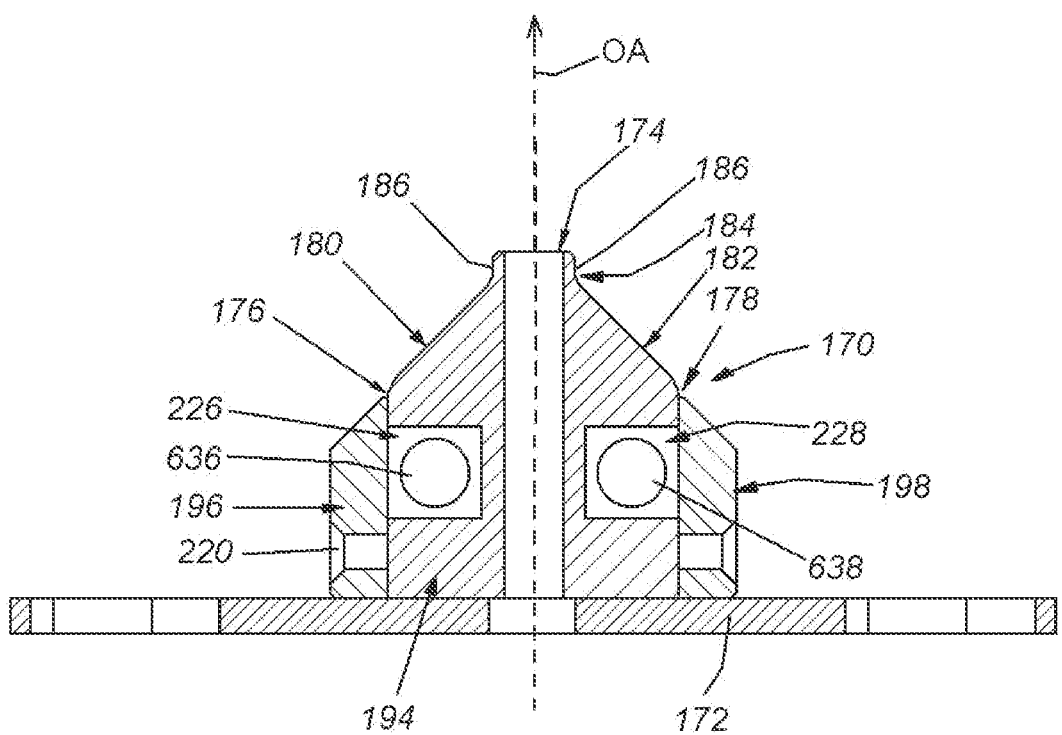
FIG. 3 is a side cross section of the air knife assembly taken along line 2-2 of FIG. 1.
Figure 4:
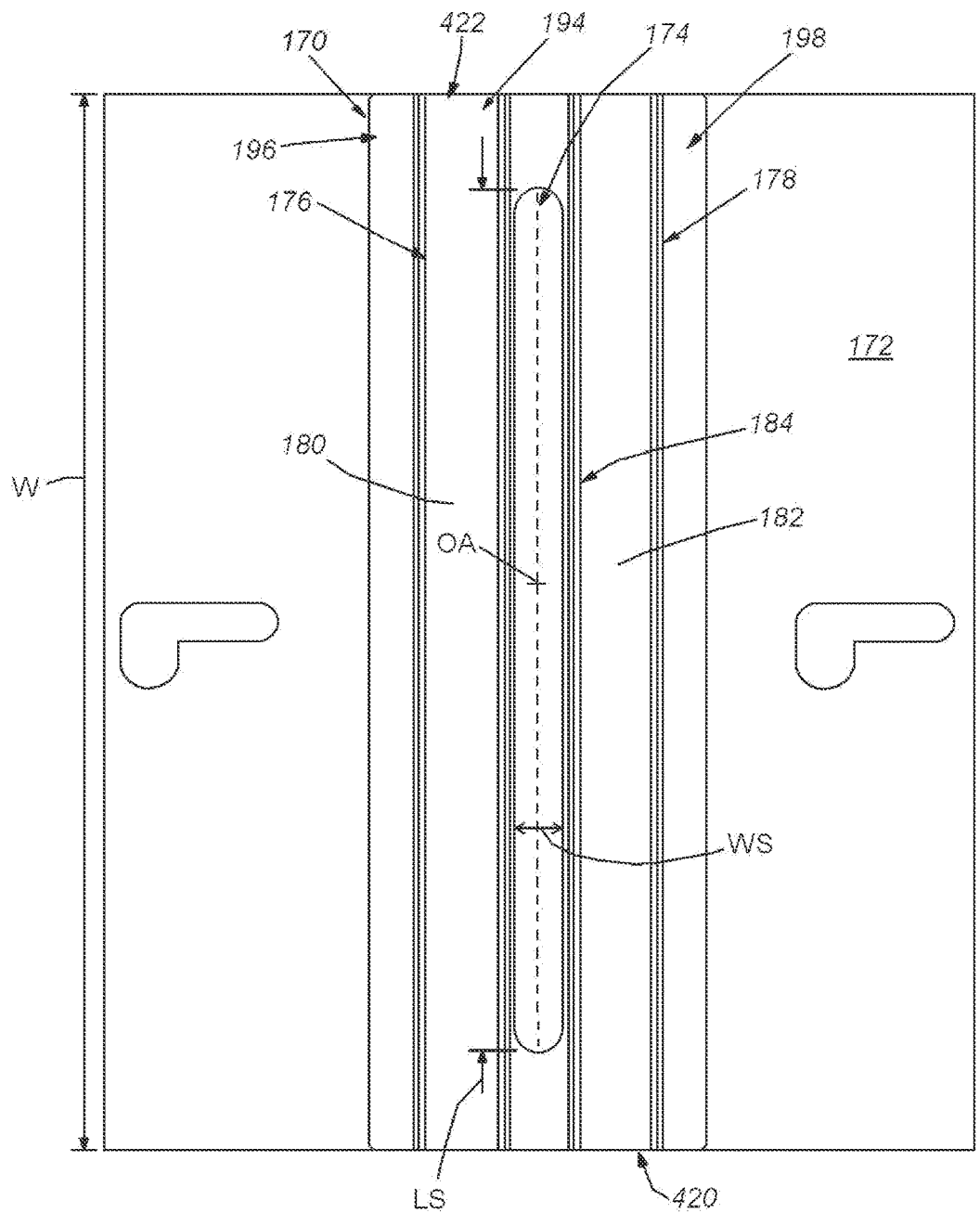
FIG. 4 is a top view of the air knife assembly of FIG. 1.

FIG. 1 shows a vision system 100 consisting of a camera assembly 110 of any acceptable size, shape and type (e.g. a line scan camera with 1D sensor 112). The camera 110 in this embodiment extends along the width W of a viewing area through which a surface 130 and/or object passes in relative motion M with respect to the camera 110. Note that either the camera 110, or the surface 130 (or both) can move along the direction of motion M. Motion M is tracked and reported to the system 100 based upon an encoder 132 that can be operatively connected to the surface drive mechanism and/or the drive motor electronics (not shown). The encoder provides pulses or equivalent data 134 with respect to predetermined physical length increments of motion (M). In alternate embodiments, the encoder 132 can be substituted with another type of motion tracking/reporting system, such as a visual tracking system based upon reading of surface marks or other surface features that pass trough the field of view of an optical detector. The camera assembly 110 also includes an appropriate lens 140 (for example a cylindrical lens) that focuses light from the surface 130 onto the sensor 112.

The camera assembly 110 is operatively connected and communicates with a processor arrangement 150 that can be onboard or remote, and connected via a wired or wireless link 152. The processor can be a purpose-built unit, such as an ASIC or FPGA or can be part of a general purpose computing platform, such as a PC, tablet or handheld device. The processor 150 runs various operating system functions and software applications, which can include a vision system process application 153, such as Patmax®, available from Cognex Corporation of Natick, Mass. Note, as used herein the terms "process" and/or "processor" should be taken broadly to include a variety of electronic hardware and/or software based functions and components. Moreover, a depicted process or processor can be combined with other processes and/or processors or divided into various sub-processes or processors. Such sub-processes and/or sub-processors can be variously combined according to embodiments herein. Likewise, it is expressly contemplated that any function, process and/or processor herein can be implemented using electronic hardware, software consisting of a non-transitory computer-readable medium of program instructions, or a combination of hardware and software. The vision system process 153 can run a variety of tools and other vision functions. For example, an inspection process can include defect-finding algorithms/processes. These processes can, in turn can employ various edge detectors, blob tools, etc. that search for anomalous and/or undesirable features on the surface. Functions can be carried out based upon input parameters that can include synthetic and model-based training data.

The processor 150 receives encoder/motion-tracking data 134 and employs this data in registering acquisition of images of the scene containing the surface 130. Such registration, as well as other functions performed by the vision system, can occur in accordance with conventional techniques known to those of skill. The processor 150, and vision system process 153, generates various image-based data (results) that can include alerts, measurements, accept/reject signals, etc. For example, in the depicted surface inspection application, the data 154 can include alarms or alerts that indicate the location and extent of a detected defect on the surface 130.

According to an illustrative embodiment, the camera's optical system is aligned along an optical axis (optical plane, extending along the width direction). The optical system is, likewise, aligned with an air knife assembly 170 in accordance with an illustrative embodiment. In this embodiment, the air-knife assembly 170 includes a mounting plate 172. This plate 172 facilitates attachment to various surfaces. In other embodiments, the mounting plate 172 can be omitted (see FIG. 5) and the overall camera 110 and air knife unit 170 can be mounted directly to a supporting surface so as to image a scene that includes an object and/or surface under inspection. Notably, the air knife assembly includes a through-slot 174 that provides an appropriately shaped and sized clearance channel so that the optics 140 can fully image the scene. The air knife assembly 170 can be constructed from a variety of materials and/or combination of materials—for example cast and/or machined aluminum alloy, polymer or composite.

In operation, and as depicted in FIG. 1, the air knife assembly 170 channels airflow AF from each of opposing slot-like passage 176 and 178 that are narrow and elongated, and extend along the approximate width of the assembly 170 on each of opposing sides of the axis (plane) OA. The airflow AF passes from each passage 176 and 178, along the respective "angled" surface 180 and 182 of the air knife assembly 170 based upon the so-called Coanda effect. The airflow AF travels along each angled surface 180, 182 until it reaches the slot base 184 and its associated vertical walls 186 at which the airflow is redirected upwardly on each opposing side of the axis/plane OA. Based upon the Coanda effect and general direction of airflow AF, the air (arrows 188) in proximity to the surfaces 180, 182 is carried along the upward path, causing a multiplying effect that generates a relatively wide region of flowing air in the region of the slot 174 and associated field of view (FOV). This overall moving air mass 188 splits any cloud or stream of contaminants C and provides a clearance area 190 in the region of the field of view. This clearance extends from the slot 174 to a location at or proximate to the object surface 130 so that the slot and underlying optics remain free of contamination and accretion of debris/contaminants.

With further reference to FIGS. 2-6, the construction of the air knife assembly and attachment to an air pressure (or other gas, e.g. nitrogen, argon, carbon dioxide, etc.) is shown in further detail. The air knife assembly 170, in this embodiment, comprises a central core 194 with a pair of opposing side members 196 and 198 that each extend the overall width W (FIG. 4) of the assembly 170. The side members 196 and 198 are each removably attached to the central core 194 by fasteners 220, or any other appropriate attachment mechanism. Note that the core 194 and side members 196, 198 can be constructed alternatively as a single unitary construction, using a variety of formation techniques including 3D printing, casting, molding and/or computerized machining. The side members 196 and 198 create an outer wall for each respective slot-like air passage 176 and 178. The geometry of the joint between the confronting walls of the core 194 and each side member 196, 198 is arranged to provide a passage for pressurized air from a respective air chamber 226, 228 out of the respective air passage 176, 178 along the approximate width of the assembly 170. Each air chamber 226, 228 in this embodiment comprises a rectangular-cross-section cavity that extends the approximately width W of the assembly 170, and extends beyond the length LS of the slot 174. In this manner, the airflow (AF in FIG. 1) generated by each air passage 176, 178 overlaps the opposing ends of the slot 174, ensuring full coverage and protection of the slot 174 from contamination. The degree of extension in each direction of the passages 176, 178 can be approximately 1-2 centimeters beyond the ends of the slot 174. The width of the passage (in the motion direction orthogonal to assembly width 170) can be approximately 0-0.1-0.2 millimeters, more or less. However, the size can vary up to approximately 1-2 millimeters in alternate embodiments.

Figure 6:
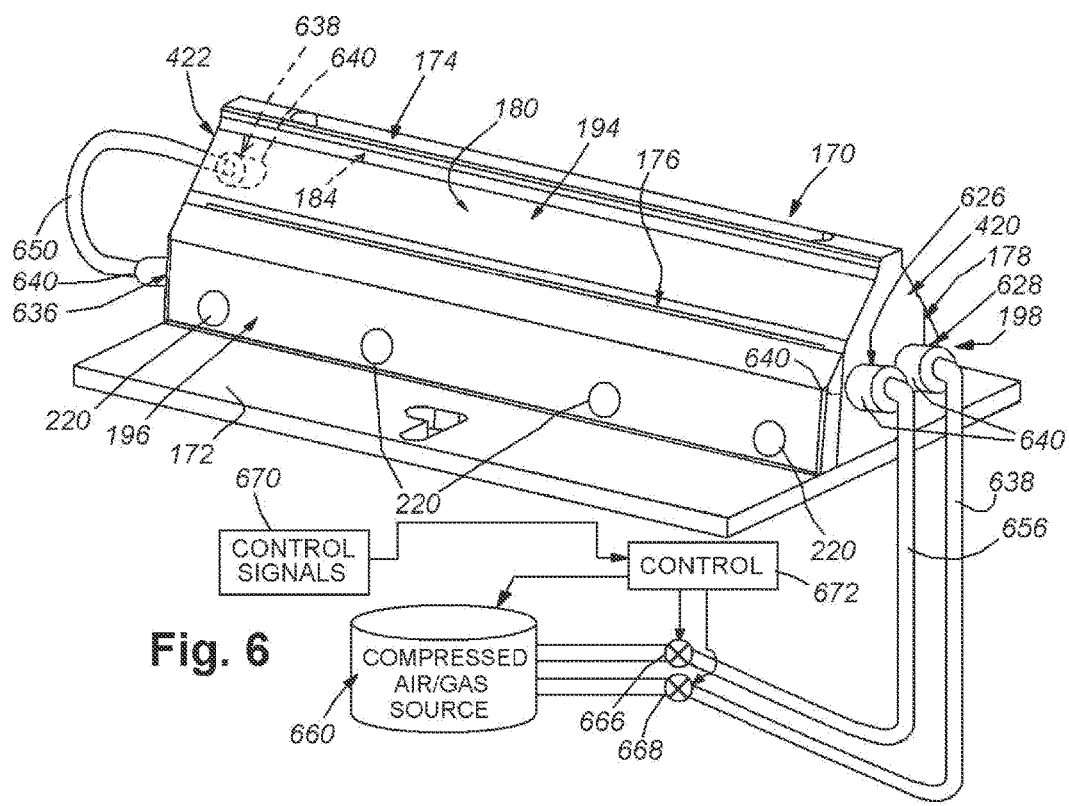
FIG. 6 is a perspective view of the air knife of FIG. 1 interconnected with a compressed air/gas source according to an illustrative embodiment.

Each air chamber 226, 228 is sealed at opposing end walls 420, 422 (FIG. 4) of the core 194, with an associated port 626, 628, 636 and 638 (FIG. 6) at each end. The ports are fitted with appropriate fluid/air connections or fittings—for example press fit bases 640 for polymer tubing—as shown in FIG. 6. Note that the arrangement of ports and fittings is exemplary, only and can be varied in alternate embodiments. For example, in an alternate embodiment, ports can be provided to only one end of chamber. As shown in FIG. 6, the ports 636, 638 along the end wall 422 are interconnected via a bridging 650, while the ports 626, 628 along opposing end wall 420 are each connected via respective tubes (i.e. gas/fluid conduits) 656, 658 to a pressure source (e.g. an air tank and/or compressor) 660. Each (or both) of the tubes can be independently regulated (on, off, pressure) via a respective valve assembly 666, 668. The valve assembly(ies) 666, 668 can be manually set, or automatically controlled by, for example, an electromechanical actuator that is controlled by an appropriate controller 672 based on control signals 670 that can be issued by the operator, or automatically provided. Illustratively, control signals to open the valves (and/or activate the source 660) can be issued in response to initialization of motion M or other production activities. Likewise, control signals can be issued upon startup of the vision system 100.

Figure 5:
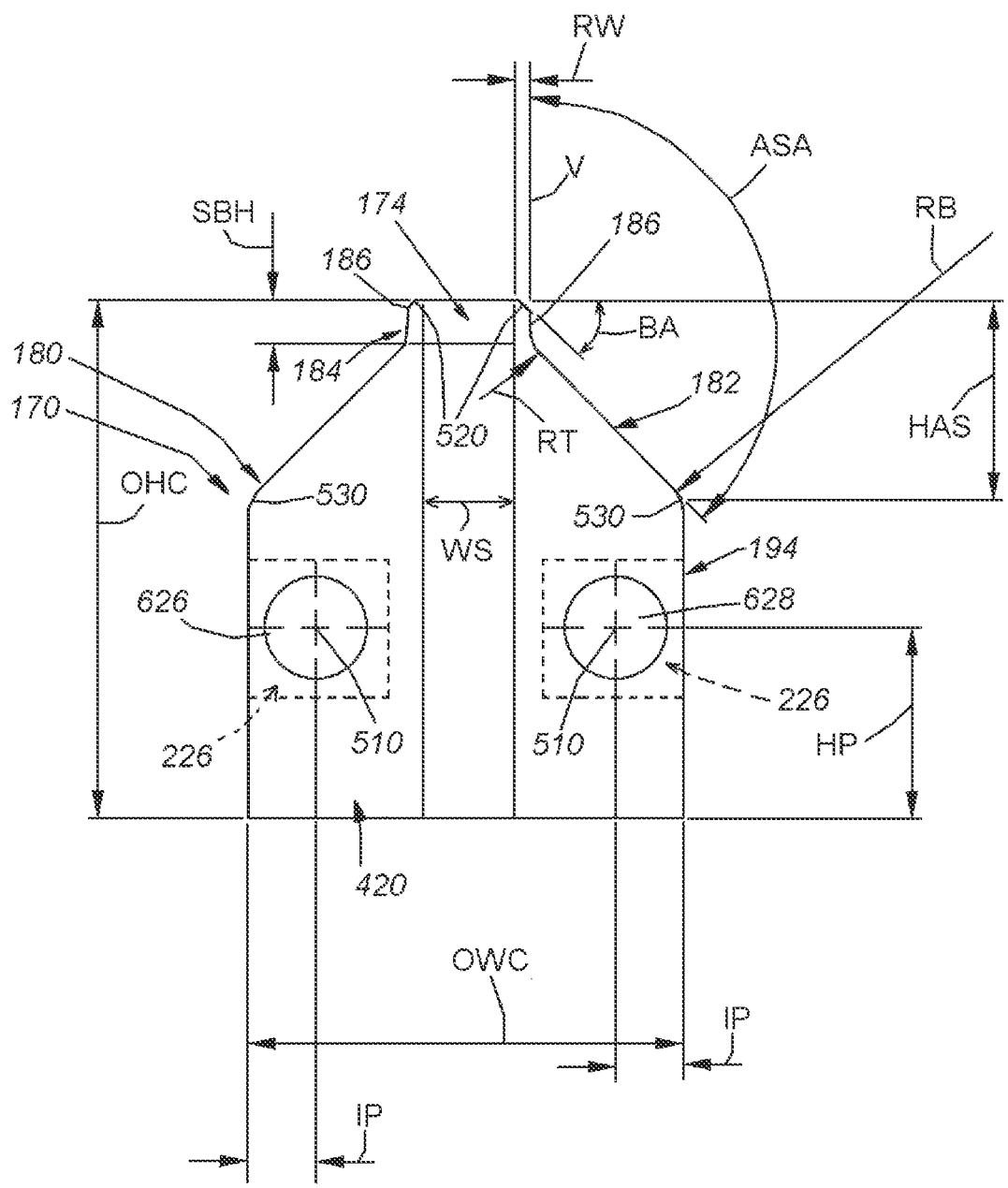
FIG. 5 is a side view of the central core of the air knife assembly of FIG. 1 showing relative dimensions of its geometry according to an illustrative embodiment.

As described generally above, the geometry of the surfaces 180 and 182 and other aspects of the air knife assembly 170 contribute to the characteristic of the airflow AF and generation of the Coanda effect. In an illustrative embodiment, and by way of non-limiting example, as shown in FIG. 5 the overall height OHC of the assembly core 194 is approximately 60 millimeters (to the top of the slot base 184). The overall width OWC (along the motion (M) direction) is approximately 50 millimeters. The center 510 of each air chamber 226, 228 is inset a distance IP of approximately 8 millimeters. Each air chamber center 510 is elevated from the core base by a distance HP of approximately 202 millimeters and the chambers are approximately 16 millimeters square. These dimensions are highly variable in alternate embodiments as is the size and shape of each air chamber 226, 228. The slot base 184 has an approximate height SBH from the top thereof of approximately 5 millimeters. The outermost edge of each side of the slot defines a bevel 520 with a bevel angle BA of approximately 45 degrees with respect to the assembly's vertical/horizontal plane. The bevel has a width (as depicted) BW of approximately 1 millimeter. The height HAS between the slot base top (the top of the core 194) and the bottom edge 530 of each angled surface 180, 182 is approximately 23 millimeters. Likewise, the angle ASA of each surface 180, 182 with respect to the vertical plane V is approximately 135 degrees, or 45 degrees relative to the core's side wall plane.

Notably, the top and bottom edges of the angled surfaces 180, 182 each define a radius RT and RB (respectively) with respect to the adjacent vertical surface. This radius particularly facilitates direction of the airflow in a desired direction. In an illustrative embodiment each radius is approximately 5-10 millimeter and an arc angle between 45° to 90°.

The width W of the air knife assembly 170 and dimensions WS and LS of the slot 174 are highly variable, and can be adapted to the size of the particular vision system camera and/or field of view (e.g. the width of the surface in a line-scan embodiment). By way of non-limiting example, the depicted embodiment has an overall width W of approximately 210 millimeters, a slot length LS of approximately 180-200 millimeters and a slot width WS of approximately 10-14 millimeters.

In operation, and more particularly, the air flow produced at each side of the air knife assembly is redirected along the convex (radiused) surface RB from the slot-like air flow passage (which can have a relatively narrow width—for example 0.1-0.2 millimeter, as described above). Thus the air flow does not travel in its original upward direction, but rather moves along the angled surface of the air knife body. In this manner, the air knife generates a curtain of air along its angled shape up to the second radius RT, adjacent to the viewing slot. The Coanda effect causes air to be drawn in from the surrounding atmosphere to augment the flow generated along the knife surface. This effectively increases/amplifies the volume of supplied compressed air by approximately twenty-five times per air knife side (or fifty times, given both sides operating together).

While the air knife assembly 170 as shown, for example, in FIG. 1 is depicted with air flow provided on both sides (i.e. from both slot-like passages 176 and 178), it is contemplated that the assembly can be controlled so that airflow (AF) is provided from only one side. This can be desirable where contaminants are infiltrating the field of view from predominantly one side or where reduced airflow is sufficient to deflect oncoming contaminants. The Coanda effect generates significant airflow with even a single side activated.

Note as used herein the term "angled surface" refers to any surface that allows air flow to be guided in an inwardly and upwardly tapered manner toward a smaller slot or port through which optics image a scene. The surface can define a planar and/or curvilinear surface profile—for example a semi-circular, parabolic or hyperbolic cross section shape.

In other illustrative embodiments, an air knife assembly in accordance with the general teachings herein can be adapted to interconnect with other assemblies to define an elongated width for scanning across a wide surface. The slot for providing a viewing clearance (for the camera optics) can be substantially continuous across the width so that it defines an unbroken aperture. One or more camera assemblies can be arranged beneath the line of air knives to provide a substantially continuous image-acquisition arrangement. The air knives can be arranged so that their air connections are secured in series, or separate air source tubes can be tied to discrete air knife assemblies in the overall, elongated arrangement. Alternatively, a single elongated air knife assembly in accordance with the teachings herein can be adapted to mount a plurality of image sensors and associated optics in a series with respect to an elongated slot. Thus, as defined herein the term "camera assembly" can include a plurality of image sensors arranged in a line with respect to a single air knife.

Note that the depicted camera assembly 110 and vision system arrangement 100 are exemplary of a wide variety of possible arrangements that are suited to the given manufacturing, inspection, ID (symbology code) reading, robot-manipulation, or other process that employs the functionality a vision system. In general, any application in which harsh conditions, contaminants, and the like, occur can benefit from the illustrative air knife arrangement 170 in accordance with embodiments herein. The geometry of the air knife (e.g. its footprint) can be adapted to the particular size and shape of the camera and optics over which it is mounted.

The following table reports experimental results in connection with the air knife arrangement described and depicted above. This table displays the detected Speed of the airflow stream (in meters/minute) and the Width (along the motion direction M) of the airflow stream (in millimeters) for each of a plurality of pressure settings. This chart is based upon the use of both passages to expel airflow.

| Distance (mm) | | 50 | 150 | 300 | 450 |
|---|---|---|---|---|---|
| Pressure in bar Speed | 0.7 | 297 | 251 | 175 | 145 |
| Width | | 12.7 | 63.5 | 127 | 146.1 |
| Pressure in bar Speed | 1.4 | 419 | 381 | 335 | 290 |
| Width | | 19.1 | 50.8 | 101.6 | 114.3 |
| Pressure in bar Speed | 2.1 | 556 | 533 | 503 | 427 |
| Width | | 25.4 | 57.2 | 108 | 120.7 |
| Pressure in bar Speed | 2.8 | 846 | 111 | 655 | 579 |
| Width | | 44.5 | 63.5 | 120.7 | 139.7 |
| Pressure in bar Speed | 4.1 | 1676 | 1402 | 975 | 914 |
| Width | | 50.8 | 69.9 | 133.4 | 190.5 |
| Pressure in bar Speed | 5.5 | 2225 | 1935 | 1387 | 1280 |
| Width | | 57.2 | 69.9 | 139.7 | 203.2 |
| Pressure in bar Speed | 6.9 | 2804 | 2377 | 1722 | 1585 |
| Width | | 63.5 | 76.2 | 146.1 | 209.6 |

It should be clear that the air knife assembly described above in accordance with various embodiments provides an effective mechanism for reducing or eliminating contamination and/or occlusion of the optics and field of view. The mechanism uses a relatively low cost and efficient medium (i.e. compressed air) and exhibits substantial reliability in a harsh environment and under long-term usage.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments of the apparatus and method of the present invention, what has been described herein is merely illustrative of the application of the principles of the present invention. For example, as used herein various directional and orientational terms such as "vertical", "horizontal", "up", "down", "bottom", "top", "side", "front", "rear", "left", "right", and the like, are used only as relative conventions and not as absolute orientations with respect to a fixed coordinate system, such as gravity. Additionally, while the depicted base plate is shown according to an embodiment, the mounting of the air knife assembly with respect to a camera assembly and/or a supporting surface can be implemented using a variety of mechanisms including various mounting holes, fasteners, clamps, brackets, and the like. Such mechanisms can be provided to the bottom/base of the air knife assembly or to another location thereon. Also, since a variety of gasses and/or fluids can be employed to generate "air flow" in accordance with embodiments, the term "air" as used herein shall refer to an acceptable substance that can generate the desired effect. Likewise, the material used to construct some or all of the elements of the air knife assembly can be widely varied. For example all or portions of the assembly can be constructed from a transparent and/or translucent material and can incorporate illumination elements and/or viewing windows, as well as lensmatic/prismatic structures to alter the received light and/or illumination pattern. By way of example, the "slot" can include a transparent covering or can be a unitary transparent window that is part of the overall air knife body. Accordingly, this description is meant to be taken only by way of example, and not to otherwise limit the scope of this invention.

What is claimed is:

1. A vision system for imaging a scene containing contaminants comprising:
    a camera assembly having an image sensor, and optics that define an optical axis and a field of view; and
    an air knife assembly having:
        (a) a first angled surface on an exterior face of the air knife assembly exposed to unpressurized ambient air, the first angled surface extending inwardly and upwardly from a bottom of the first angled surface to a top of the first angled surface, (b) a slot defined in part by a second surface on the exterior face of the air knife assembly exposed to the unpressurized ambient air, the second surface opposed to the first angled surface, the slot extending through an interior of the air knife assembly along the optical axis so as to allow the scene to be imaged through the slot, and (c) a first air flow passage located on the exterior face of the air knife assembly exposed to the unpressurized ambient air adjacent to the bottom of the first angled surface, and the bottom of the first angled surface being constructed and arranged to direct pressurized air flow from the first air flow passage along the exterior face of the first angled surface, the top of the first angled surface being constructed and arranged to redirect the pressurized air flow from the exterior face of the first angled surface into the field of view, and the pressurized air flow flowing along the exterior face of the air knife assembly causing ambient air external to the air knife assembly to be carried along with the pressurized air flow into the field of view.

2. The vision system as set forth in claim 1 further comprising a vision system processor operatively connected to the image sensor for performing vision system tasks on image data transmitted from the image sensor.

3. The vision system as set forth in claim 1 wherein the air knife assembly has a second angled surface, on an opposite side with respect to the optical axis from a side having the first angled surface, the second angled surface extending inwardly and upwardly from a bottom of the second angled surface to a top of the second angled surface, and a second air flow passage located adjacent to the bottom of the second angled surface, and the bottom of the second angled surface being constructed and arranged to direct air flow from the second air flow passage along an exterior face of the second angled surface and the top of the second angled surface being constructed and arranged to redirect air flow from the exterior face of the second angled surface into the field of view.

4. The vision system as set forth in claim 3 wherein the first angled surface and the second angled surface are each located on a core section, the core section being operatively connected to (a) a first side member that defines the first air flow passage and (b) a second side member that defines the second air flow passage.

5. The vision system as set forth in claim 4 wherein (a) the first side member overlies a first air chamber within the core section, the first air chamber extending at least part of a length of the core section and (b) the second side member overlies a second air chamber within the core section, the second air chamber extending at least part of a length of the core section on a side of the slot opposite the first air chamber.

6. The vision system as set forth in claim 5 wherein at least one of the first air chamber and the second air chamber is operatively connected to a conduit that directs pressurized air into the at least one of the first air chamber and the second air chamber.

7. The vision system as set forth in claim 1 wherein the top of the first angled surface defines a first radius and the bottom of the first angled surface defines a second radius.

8. The vision system as set forth in claim 7 wherein the top of the first angled surface is connected to a vertical wall that confronts the slot the vertical wall extending upwardly from the first radius.

9. The vision system as set forth in claim 8 wherein the vertical wall defines a bevel at a top edge thereof.

10. The vision system as set forth in claim 1 wherein the camera assembly comprises a line scan camera and the image sensor comprises a 1D sensor.

11. The vision system as set forth in claim 10 wherein the line scan camera is constructed and arranged to scan a surface in relative motion with respect to the line scan camera.

12. An air knife assembly for a vision system having an image sensor and optics that define an optical axis comprising:

an air knife body having:

(a) a first angled surface on an exterior face of the air knife assembly exposed to unpressurized ambient air, the first angled surface extending inwardly and upwardly from a bottom of the first angled surface to a top of the first angled surface, (b) a slot defined in part by a second surface on the exterior face of the air knife assembly exposed to the unpressurized ambient air, the second surface opposed to the first angled surface, the slot extending through an interior of the air knife body along the optical axis so as to allow the scene to be imaged through the slot, and (c) a first air flow passage located on the exterior face of the air knife assembly exposed to the unpressurized ambient air adjacent to the bottom of the first angled surface, and the bottom of the first angled surface being constructed and arranged to direct pressurized air flow from the first air flow passage along the exterior face of the first angled surface and the top of the first angled surface being constructed and arranged to redirect the pressurized air flow from the exterior face of the first angled surface into the field of view, and the pressurized air flow flowing along the exterior face of the air knife assembly causing the unpressurized ambient air external to the air knife assembly to be carried along with the pressurized air flow into the field of view.

13. The air knife assembly as set forth in claim 12 wherein the air knife body has a has a second angled surface, on an opposite side with respect to the optical axis from a side having the first angled surface, the second angled surface extending inwardly and upwardly from a bottom of the second angled surface to a top of the second angled surface, and a second air flow passage located adjacent to the bottom of the second angled surface, and the bottom of the second angled surface being constructed and arranged to direct air flow from the second air flow passage along an exterior face of the second angled surface and the top of the second angled surface being constructed and arranged to redirect air flow from the exterior face of the second angled surface into the field of view.

14. The air knife assembly as set forth in claim 13 wherein the first angled surface and the second angled surface are each located on a core section of the air knife body, the core section being operatively connected to (a) a first side member that defines the first air flow passage and (b) a second side member that defines the second air flow passage.

15. The air knife assembly as set forth in claim 14 wherein (a) the first side member overlies a first air chamber within the core section, the first air chamber extending at least part of a length of the core section and (b) the second side member overlies a second air chamber within the core section, the second air chamber extending at least part of a length of the core section on a side of the slot opposite the first air chamber.

16. The air knife assembly as set forth in claim 15 wherein at least one of the first air chamber and the second air chamber is operatively connected to a conduit that directs pressurized air into the at least one of the first air chamber and the second air chamber.

17. The air knife assembly as set forth in claim 12 wherein the top of the first angled surface defines a first radius and the bottom of the first angled surface defines a second radius.

18. The air knife assembly as set forth in claim 17 wherein the top of the first angled surface is connected to a vertical wall that confronts the slot the vertical wall extending upwardly from the first radius.

19. The air knife assembly as set forth in claim 12, wherein the first angled surface is positioned between the resulting air flow and the slot arranged along the optical axis.

20. An air knife assembly for a vision system having an image sensor and optics comprising:

an air knife body defining an angled side on an exterior face of the air knife assembly exposed to unpressurized ambient air, the air knife body having an air flow passage at the bottom of the angled side on the exterior face of the air knife assembly exposed to the unpressurized ambient air and an edge at the top of the angled side that confronts an opening defined in part by a second side opposed to the angled side through which the optics images a scene in a field of view, the body being constructed and arranged to direct pressurized air flow along the exterior face of the air knife assembly causing the unpressurized ambient air external to the air knife assembly to be carried along with the pressurized air flow into the field of view so as to deflect contaminants and debris from the opening.

21. The vision system set forth in claim 1, wherein the first angled surface is positioned between the resulting airflow and the slot arranged along the optical axis.

22. The air knife assembly of claim 20, wherein the angled side is disposed between the opening and the air flow.

* * * * *